(12) United States Patent
Fujikawa et al.

(10) Patent No.: US 11,806,511 B2
(45) Date of Patent: Nov. 7, 2023

(54) AUTO INJECTOR DEVICE (71) Applicants: Amana Fujikawa, Tokyo (JP); Erika Robottom, Tokyo (JP); Emi Sun, Tokyo (JP); Debangi Mohanta, Tokyo (JP); Sofyani Tatipamula, Tokyo (JP)

(72) Inventors: Amana Fujikawa, Tokyo (JP); Erika Robottom, Tokyo (JP); Emi Sun, Tokyo (JP); Debangi Mohanta, Tokyo (JP); Sofyani Tatipamula, Tokyo (JP)

( * ) Notice: Subject to any disclaimer, the term of this patent is extended or adjusted under 35 U.S.C. 154(b) by 229 days.

(21) Appl. No.: 16/817,975

(22) Filed: Mar. 13, 2020

(65) Prior Publication Data

US 2020/0289756 A1 Sep. 17, 2020

Related U.S. Application Data

(60) Provisional application No. 62/817,576, filed on Mar. 13, 2019.

(51) Int. Cl.
*A61M 5/20* (2006.01)
*A61M 5/32* (2006.01)

(52) U.S. Cl.
CPC ........ *A61M 5/2033* (2013.01); *A61M 5/3202* (2013.01); *A61M 2005/2073* (2013.01); *A61M 2205/18* (2013.01); *A61M 2205/3553* (2013.01)

(58) Field of Classification Search
CPC .............. A61M 5/2033; A61M 5/3202; A61M 2005/2073; A61M 2205/18; A61M 2205/3553; A61M 5/003

USPC ......................................................... 604/135
See application file for complete search history.

(56) References Cited

U.S. PATENT DOCUMENTS

| | | | | |
|---|---|---|---|---|
| 2003/0199814 | A1* | 10/2003 | Parsons | A61M 5/30 604/68 |
| 2008/0306436 | A1* | 12/2008 | Edwards | G16H 40/20 604/87 |
| 2011/0083445 | A1* | 4/2011 | Heyd | A61M 5/14244 62/3.3 |
| 2014/0039383 | A1* | 2/2014 | Dobbies | A61B 5/7475 604/66 |
| 2015/0290392 | A1* | 10/2015 | Henderson | A61M 5/3204 604/111 |

(Continued)

*Primary Examiner* — Katherine H Schwiker
*Assistant Examiner* — Nidah Hussain
(74) *Attorney, Agent, or Firm* — ARENTFOX SCHIFF LLP (57) ABSTRACT

Aspects of an auto injector device are provided which allow for increased reusability, portability and convenience, thermal insulation, and safety. The auto injector device is encapsulated in a case for a mobile communications device and includes a cartridge, an outer casing fixed to the case and attached to the cartridge and including a piston, and a sensor attached to the case. The cartridge is configured to contain a fluid and includes a needle. The piston is configured to pump the fluid in the cartridge through the needle in response to application of a force during injection of the auto injector device. The cartridge is detachable from the outer casing. The sensor is in wireless communication with an emergency alert system, and the sensor is configured to sense movement of the needle and to communicate with the emergency alert system in response to application of the force during the injection.

19 Claims, 8 Drawing Sheets

(56) References Cited

U.S. PATENT DOCUMENTS

2016/0193408 A1* 7/2016 Schweikert ........... A61M 5/178
                                                      604/500
2017/0007765 A1* 1/2017 Cowe .................... A61M 5/172

* cited by examiner

818 — Detach Removable Cartridge From Outer Casing Through Case

820 — Reset Spring Using Spring Compression Tool

822 — Re-Attach Safety Hook To Spring

824 — Attach Replacement Cartridge To Outer Casing Through Case

FIG. 8B

AUTO INJECTOR DEVICE

CROSS-REFERENCE TO RELATED APPLICATION(S)

This application claims the benefit of U.S. Provisional Application Ser. No. 62/817,576, entitled "eSecure" and filed on Mar. 13, 2019, which is expressly incorporated by reference herein in its entirety.

BACKGROUND

Field

The disclosure is generally related to injection devices and more particularly to an auto injector device.

Introduction

Millions of people suffer from allergies every year, and hundreds of thousands of people may experience severe allergic reactions to certain food types. Many people may also suffer from anaphylaxis, a potentially life-threatening condition requiring emergency medical care for treatment. Epinephrine is a medication that is commonly used to alleviate these allergic reactions and is typically administered using an auto injector. Individuals prone to allergies may carry an auto injector with them at all times for emergencies, and pharmacies and hospitals may store numerous auto injectors for ready use.

However, epinephrine auto injectors are generally single-use only, have a short shelf life (e.g. eighteen months or less), and are commonly expensive. Therefore, these auto injectors must be frequently replaced, tend to expire before they are used, and are difficult for many individuals to afford. Epinephrine auto injectors are also generally bulky and inconvenient to carry around, and individuals may forget to carry the auto injectors with them at various times. Epinephrine must also be maintained in a narrow temperature range (e.g. optimally 15-30° C., but preferably 20-25° C.) to avoid degradation and reduced effectiveness, which may be difficult to manage for people in hotter and colder climates and seasons. Additionally, individuals who misuse epinephrine auto injectors may suffer from severe side effects, and it is possible for some individuals who inject the medication correctly to still require medical treatment.

SUMMARY

Several aspects will be described more fully hereinafter with reference to various illustrative aspects of the present disclosure.

One aspect of an auto injector device is disclosed herein. The auto injector device includes a cartridge and an outer casing attached to the cartridge and including a piston. The cartridge is configured to contain a fluid and includes a needle. The piston is configured to pump the fluid in the cartridge through the needle in response to application of a force during injection of the auto injector device. The cartridge is detachable from the outer casing.

Another aspect of an auto injector device is disclosed herein. The auto injector device is encapsulated in a case for a mobile communications device and includes a cartridge, and an outer casing fixed to the case and attached to the cartridge and including a piston. The cartridge is configured to contain a fluid and includes a needle. The piston is configured to pump the fluid in the cartridge through the needle in response to application of a force during injection of the auto injector device. The cartridge is detachable from the outer casing.

A further aspect of an auto injector device is disclosed herein. The auto injector device is encapsulated in a case for a mobile communications device and includes a cartridge, an outer casing fixed to the case and attached to the cartridge and including a piston, and a sensor attached to the case. The cartridge is configured to contain a fluid and includes a needle. The piston is configured to pump the fluid in the cartridge through the needle in response to application of a force during injection of the auto injector device. The cartridge is detachable from the outer casing. The sensor is in wireless communication with an emergency alert system, and the sensor is configured to sense movement of the needle and to communicate with the emergency alert system in response to application of the force during the injection.

It is understood that other aspects of the auto injector device will become readily apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of the present invention will now be presented in the detailed description by way of example, and not by way of limitation, with reference to the accompanying drawings, wherein.

DETAILED DESCRIPTION

The detailed description set forth below in connection with the appended drawings is intended as a description of various exemplary embodiments of the present invention and is not intended to represent the only embodiments in which the present invention may be practiced. The detailed description includes specific details for the purpose of providing a thorough understanding of the present invention. However, it will be apparent to those skilled in the art that the present invention may be practiced without these specific details. In some instances, well-known structures and components are shown in block diagram form in order to avoid obscuring the concepts of the present invention. Acronyms and other descriptive terminology may be used merely for convenience and clarity and are not intended to limit the scope of the invention.

The words "exemplary" and "example" are used herein to mean serving as an example, instance, or illustration. Any exemplary embodiment described herein as "exemplary" is not necessarily to be construed as preferred or advantageous over other exemplary embodiments. Likewise, the term "exemplary embodiment" of an apparatus, method or article of manufacture does not require that all exemplary embodiments of the invention include the described components, structure, features, functionality, processes, advantages, benefits, or modes of operation.

In the following detailed description, various aspects of an auto injector device will be presented. These aspects are well suited for auto injectors containing epinephrine. However, those skilled in the art will realize that these aspects may be extended to auto injectors containing any type of medication or other fluid. Accordingly, any reference to a specific apparatus or method is intended only to illustrate the various aspects of the present invention, with the understanding that such aspects may have a wide range of applications without departing from the spirit and scope of the present disclosure.

Epinephrine auto injectors are used to alleviate severe, life-threatening allergic reactions which users may experience. However, these auto injectors generally have a short shelf life, are typically not reusable, and must be maintained in a narrow temperature range for maximum effectiveness. As a result, epinephrine auto injectors may frequently be discarded (e.g. due to expiration, use, or degradation from higher temperatures), requiring users to restock their supply at least once a year to replace expired, used, or degraded auto injectors. As these auto injectors also tend to be expensive, many consumers may not be able to afford such frequent replacements. Conventional auto injectors are also typically bulky or inconvenient to carry around, resulting in users forgetting to have auto injectors on-hand when needed for emergency use. Additionally, users experiencing anaphylaxis who apply conventional auto injectors may refrain from necessary treatment at a hospital immediately afterwards, increasing the risk of untreated, extreme allergic reactions.

To reduce the frequency and cost of restocking auto injectors, the present disclosure provides an auto injector device which includes a replaceable cartridge of epinephrine. The cartridge is attached to an outer casing of the device including a piston, and the piston uses a spring to pump the epinephrine through a needle of the cartridge in response to application of a force during injection of the auto injector device. The force may be applied by the user, e.g. by the user thrusting the cartridge and needle against the user's thigh or another body part. After the cartridge is emptied, the user may detach the used cartridge from the outer casing and attach a replacement cartridge to the outer casing. The auto injector device may thus be reused numerous times with new cartridges without having to replace the piston, spring, or other reusable components of the device.

Moreover, to increase the convenience of carrying auto injectors, the auto injector device is compact and encapsulated in a thermally insulated case. The case may be for a mobile communications device, such as a smartphone. The case may include an inner surface made of fiberglass or other heat-resistant material which insulates the epinephrine and maintains the medication within a preferred temperature range (e.g. 20-25° C.) even in extreme temperature environments (e.g. −29 to 149° C.). The case also includes an outer surface made of polycarbonate or other highly durable material to protect the cartridge and other components of the auto injector device from being damaged from an impact of accidentally dropping the case.

The present disclosure also reduces the risk of untreated, extreme allergic reactions by automatically alerting emergency services when the auto injector device is used. A sensor in wireless communication with an emergency alert system is attached to the case for the mobile communications device. The sensor senses movement of the needle in the cartridge when the medication or other fluid is administered. In response to the sensed movement, the sensor communicates with the emergency alert system to sound an alarm and call emergency services. For example, the sensor may trigger the user's communications device in the case to output an alarm, to communicate with a Public Safety Answering Point (PSAP) (e.g. by calling 9-1-1 or some other number), and to relay the communications device's location information (e.g. GPS position) and time (e.g. a time stamp corresponding to the time of injection) to the PSAP to be routed to hospitals or other emergency services to dispatch medical personnel to the location.

In this way, the present disclosure provides auto injector reusability and saves costs by allowing users to purchase and replace only the cartridge, rather than the entire auto injector device, after the epinephrine is used or discarded. The present disclosure also reduces the frequency of restocking auto injectors and maintains the effectiveness of the epinephrine by thermally insulating the medication within the case for a user's mobile communications device. The case maintains the temperature of the epinephrine within the preferred temperature range for the medication even in hot or cold environments, thus preventing the shelf life of the auto injector from prematurely degrading. The present disclosure further increases the convenience and portability of auto injectors by fixing the various components of the auto injector device to the case for the mobile communications device, thereby minimizing the likelihood of users forgetting to bring the auto injector device with them when needed. Additionally, the present disclosure reduces the risk of users suffering from untreated, extreme allergic reactions by alerting emergency services in response to application of the auto injector device.

Figure 1:
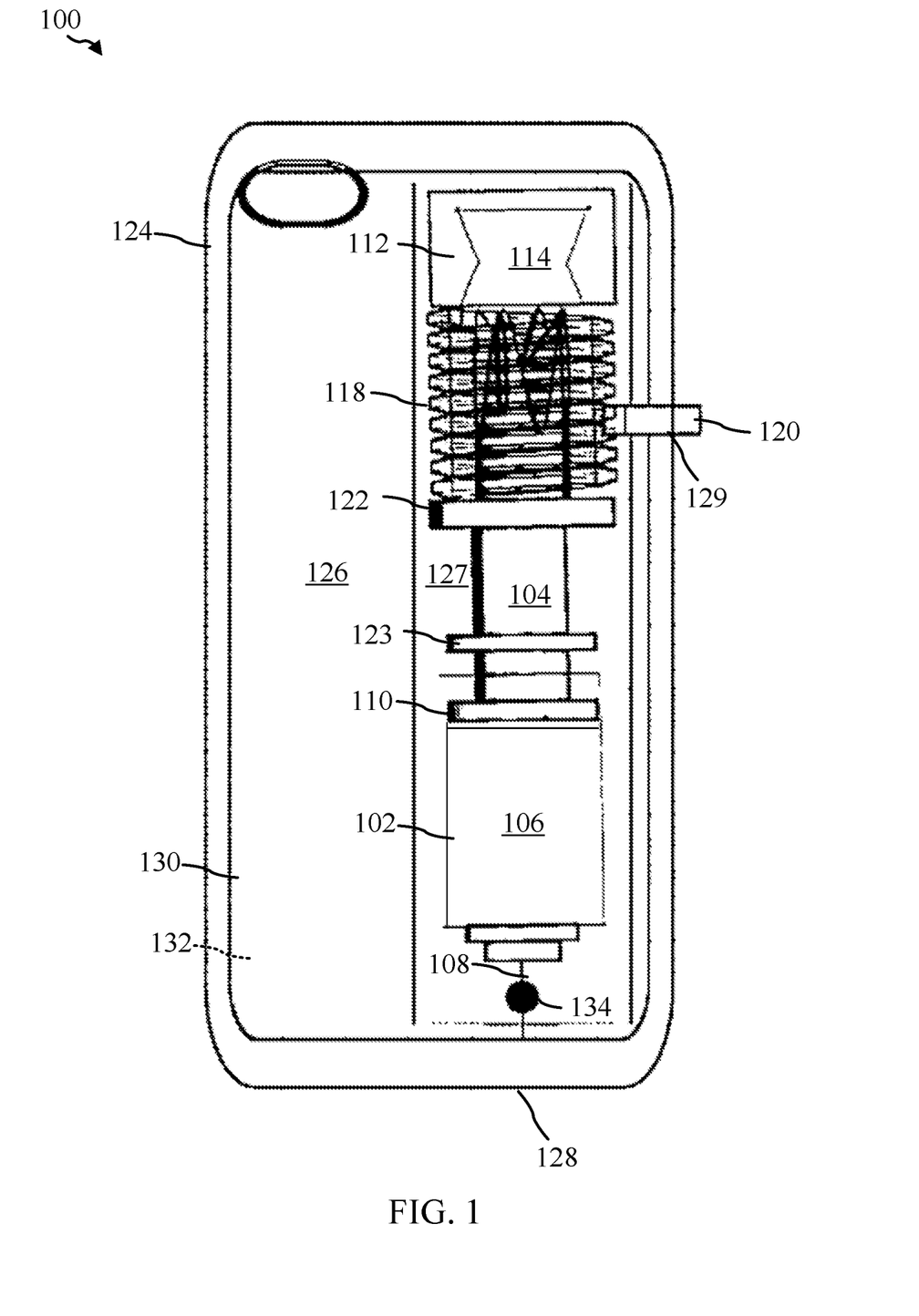
FIG. 1 is a conceptual diagram of an auto injector device including a case for a mobile communications device, a piston, spring, safety chamber, safety hook, and sensor fixed to the case, and a removable cartridge attached to the piston.
Figure 2:
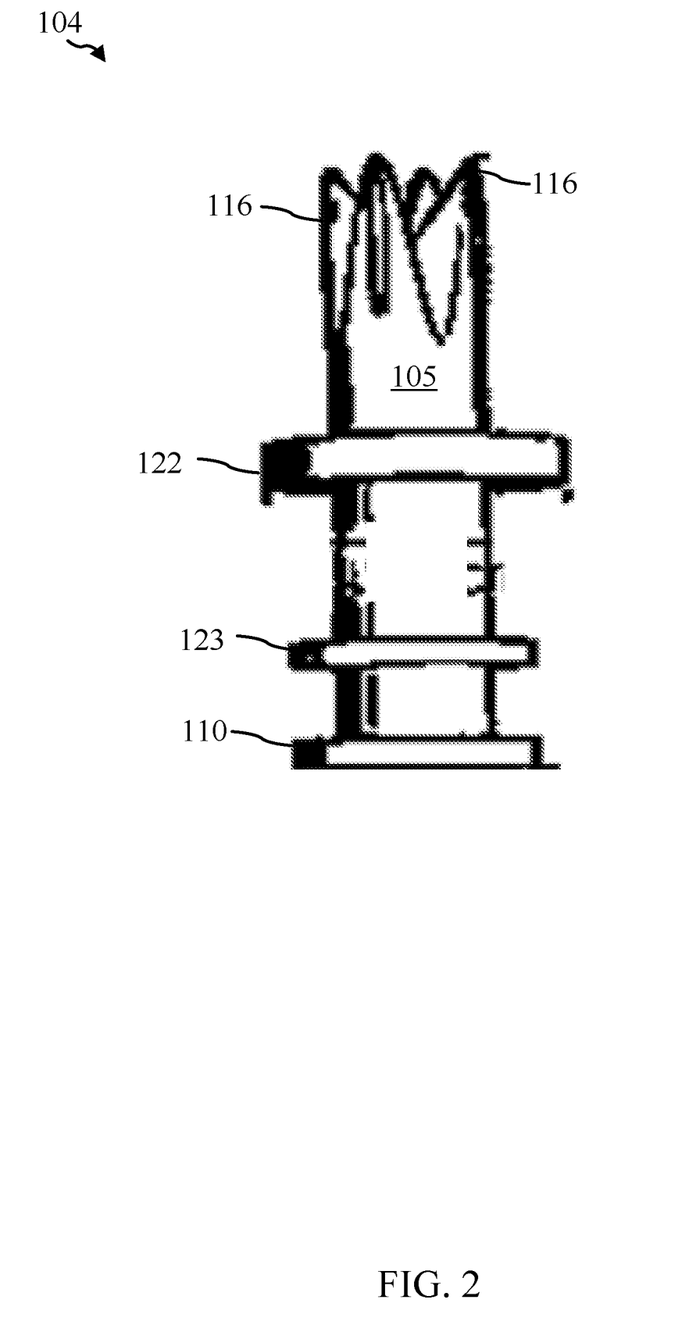
FIG. 2 is a conceptual diagram illustrating the piston of the auto injector device of FIG. 1.

FIGS. 1 and 2 illustrate an example auto injector device 100 including a cartridge 102 and a piston 104. Although not shown in FIG. 1, the piston is contained in an outer casing (see outer casing 450 of FIGS. 4A-4C) attached to the cartridge. The cartridge 102 may contain a fluid 106, such as epinephrine or another medication, and the cartridge 102 includes a needle 108 through which the fluid 106 may be dispensed. The piston 104 may be movable within the cartridge 102 to pump the fluid 106 through the needle 108. For example, the piston 104 may include a flange 110 which presses against the fluid 106 in the cartridge 102 to cause the fluid to move through the needle 108. The piston may pump the fluid through the needle in response to application of a force during injection of the auto injector device 100 (e.g. in response to forcefully applying the cartridge against a user's thigh or other injection site), as described for example below with respect to FIGS. 3A and 3B. Moreover, to provide reusability of the auto injector device 100, the cartridge 102 is detachable from the outer casing, as described for example below with respect to FIGS. 4A-4D.

The auto injector device 100 includes a safety chamber 112 disposed opposite the cartridge 102, a spring 118 disposed between the safety chamber 112 and the cartridge 102, and a safety hook 120 contacting the spring 118. The safety chamber 112 includes a recess 114 that is sized to receive a portion 105 of the piston 104 (see FIG. 2) between the safety chamber 112 and the cartridge 102. The portion 105 may include one or more projections 116 that may fit within the recess 114 of the safety chamber 112. The spring 118 may contact the portion 105 of the piston 104 including the one or more projections 116. For example, the spring 118 may circumferentially surround the portion 105, and the one or more projections 116 may extend from the piston 104 to contact and prevent movement of the spring 118. The safety hook 120 further contacts the spring 118 in addition to the one or more projections 116 to prevent movement of the spring 118. For example, the safety hook 120 may hook into the spring 118, as illustrated in FIG. 1, or may be otherwise movable between the spring and the piston.

Figure 3A:
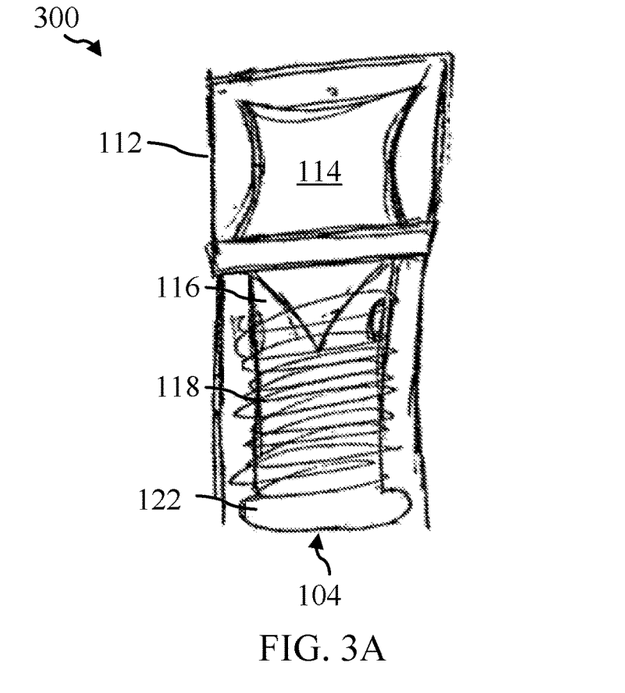
FIGS. 3A-3B are conceptual diagrams respectively illustrating the spring of the auto injector device of FIG. 1 in a compressed and expanded state.
Figure 3B:
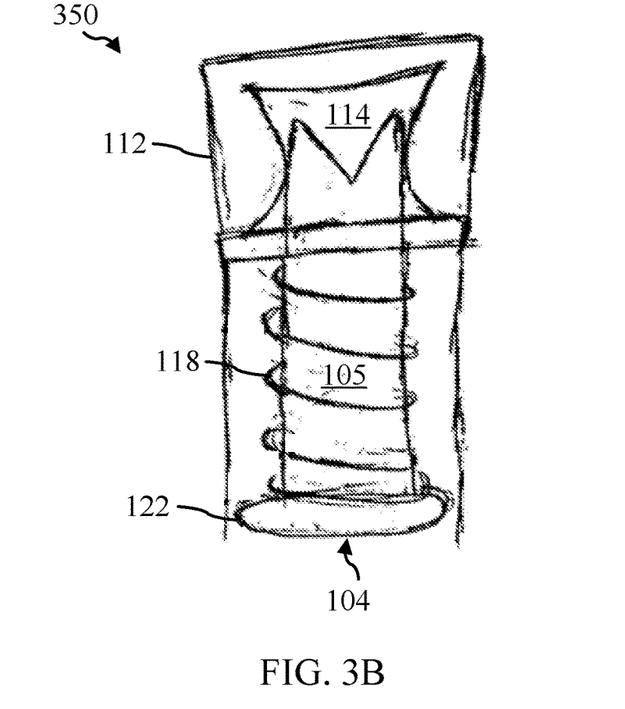

Referring to FIGS. 3A and 3B, the spring 118 may switch between a compressed state 300 (e.g. as shown in FIGS. 1 and 3A) and an expanded state 350 (e.g. as shown in FIG. 3B). The spring 118 initially is in the compressed state 300. For example, as illustrated in FIG. 3A, the piston 104 may include a flange 122 that compresses the spring 118 against the safety chamber 112. Moreover, the one or more projections 116 as well as the safety hook 120 contacting the spring 118 (see FIG. 1) may initially prevent the spring 118 from expanding away from the safety chamber 112. In one example, the spring 118 may have a length of 3 cm (or another size) when in the compressed state, and a length of 5 cm (or another size) when in the expanded state.

During operation, the user may unhook or move the safety hook 120 away from the spring 118, and the user may forcefully apply the auto injector device 100 including the cartridge 102 and needle 108 against the user's thigh or other injection site. Due to spring forces exerted by the spring 118 against the piston 104, the piston may force the cartridge 102 (e.g. using a flange 123 of the piston as illustrated in FIG. 1) towards the injection site. When the cartridge 102 is forcefully applied in this manner against the injection site, the injection site may apply an equal and opposite force against the cartridge 102 based on Newton's Third Law of Motion. As a result, the cartridge 102 may similarly apply a force against the piston 104 (e.g. against the flange 123), pushing the piston towards the safety chamber 112 and further compressing the spring 118.

At this point, the spring 118 may switch to the expanded state 350, as illustrated in FIG. 3B. For example, in response to the force applied by the injection site against the cartridge 102 (and thus the piston 104), the portion 105 of the piston 104 including the one or more projections 116 may momentarily enter the recess 114 of the safety chamber 112, away from contact with the spring 118. As a result, the spring may become free to release the tension from compression and subsequently expand away from the safety chamber 112 (e.g. against the flange 122 of the piston 104) towards the cartridge 102. In response to the expansion of the spring 118, the piston 104 may force the cartridge 102 (e.g. using flange 123) toward the injection site and pump the fluid 106 within the cartridge (e.g. via the flange 110 shown in FIG. 1) through the needle 108 into the injection site. For example, the spring 118 may be configured to have a sufficiently large wire diameter (e.g. 1.485 mm), outer diameter (e.g. 14.5 mm), free length (e.g. 50 mm), and number of active coils (e.g. 18.2) to provide sufficient force (e.g. greater than 71.2 N) to fully administer the injection. After use, the cartridge 102 may be detached from the outer casing including piston 104, as described below with respect to FIGS. 4A-4D.

Figure 4A:
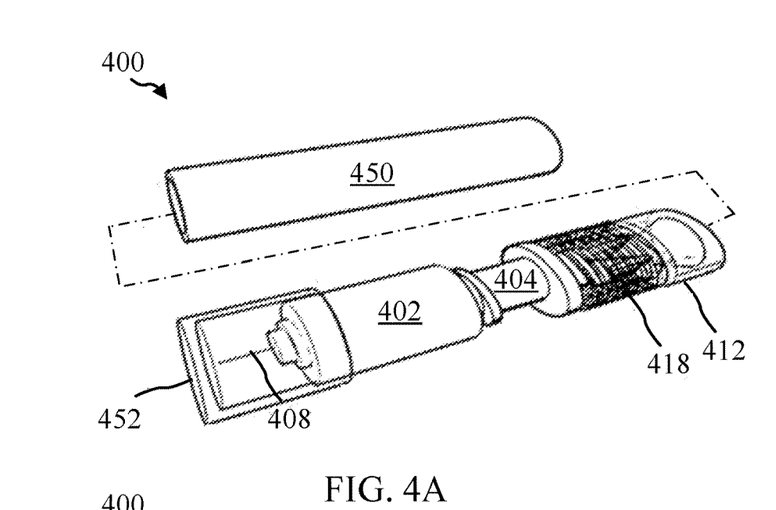
FIGS. 4A-4D are conceptual diagrams illustrating an outer casing for enclosing the piston, spring, safety chamber, and safety hook, a removable cartridge of the auto injector device of FIG. 1, and a quarter locking mechanism for attaching the cartridge to the outer casing.
Figure 4B:
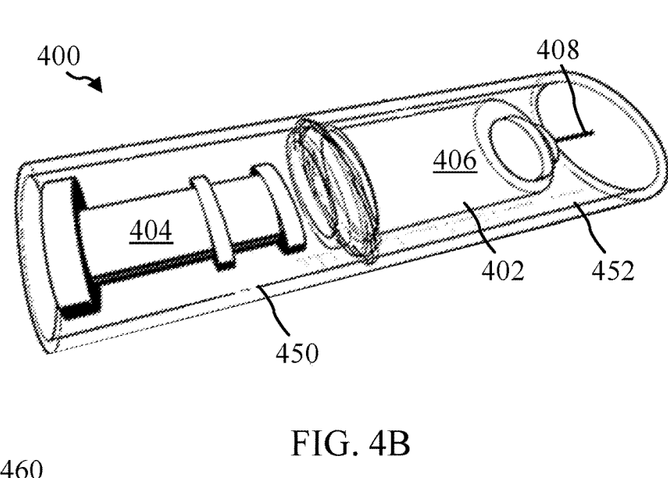
Figure 4C:
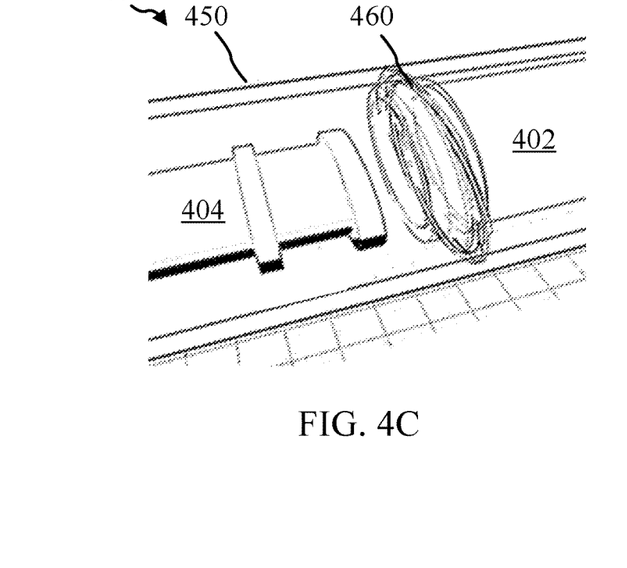
Figure 4D:
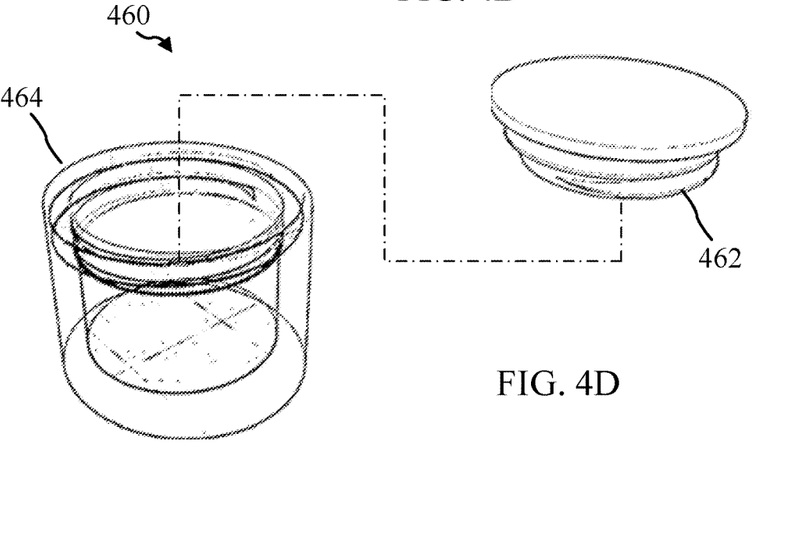

Referring to FIGS. 4A-4D, the auto injector device 400 may include an outer casing 450 which includes various components of the device, including the piston 404, the safety chamber 412, the spring 418, and the safety hook (not shown), but which does not include the cartridge 402 with fluid 406 and needle 408. In particular, FIG. 4A illustrates the various components of the auto injector device 400 removed from the outer casing 450, FIG. 4B illustrates a partial view of the components of the auto injector device 400 within the outer casing 450 and attached to the cartridge 402, FIG. 4C illustrates an enlarged view of a locking mechanism for attaching the outer casing 450 to the cartridge 402, and FIG. 4D illustrates an example configuration of the locking mechanism. The auto injector device 400 may correspond to the auto injector device 100 of FIG. 1. Similarly, the cartridge 402, piston 404, fluid 406, needle 408, safety chamber 412, spring 418, and safety hook may correspond to the cartridge 102, piston 104 (including first flange 122, second flange 123, and third flange 110), fluid 106, needle 108, safety chamber 112, spring 118, and safety hook 120 respectively shown in FIGS. 1 and 2.

As illustrated in FIG. 4B, the outer casing 450 may include the piston 404 (as well as the safety chamber 412, spring 418, and safety hook). The cartridge 402 may be detachable from the outer casing 450. For instance, the cartridge 402 and outer casing 450 may together include a quarter locking mechanism 460 (see FIG. 4C) in which the cartridge 402 may be rotated clockwise (or counterclockwise) 90 degrees with respect to outer casing 450 into locking engagement with the outer casing 450 (e.g. via threads 462, grooves 464, etc.). In this way, the cartridge 402 may be detached from the outer casing 450 after use (e.g. dispensation of the fluid as described above) or expiration, and a replacement cartridge may be similarly attached to the outer casing 450, thereby providing reusability of the auto injector device without having to discard or replace the piston, safety chamber, spring, safety hook, or other components of the outer casing after use.

As illustrated in FIG. 4A, the cartridge 402 may also include a cap 452 which covers the needle 408. The cap 452 may be sized relative to the needle 408 to facilitate use of the quarter locking mechanism. For example, the cap may be longer than the needle, as shown in FIG. 4A, such that it snugly contacts the cartridge 402. In this way, when a replacement cartridge is being attached to the outer casing 450 using quarter locking mechanism 460, the cartridge 402 may be rotated using the cap 452 into locking engagement with the outer casing 450. The cap may be subsequently removed to enable use of the needle 408. The cap 452 thus allows the cartridge 402 to be easily and safely attached to the outer casing when the auto injector device 400 is carried in an enclosure such as the case 124 described below.

Referring back to FIG. 1, the auto injector device 100 may further be encapsulated in a case 124 to which the piston 104, the spring 118, the safety chamber 112, and the safety hook 120 are fixed. The case 124 may include a first opening 126 configured to hold a mobile communications device (not shown), such as a smartphone, tablet, or the like, in addition to the other components of the auto injector device. For example, the case 124 may include a cavity 127 inside the first opening 126 in which the outer casing 450 may be attached, and the mobile communications device may be placed through the first opening 126 on top of the cavity 127 above the outer casing 450.

The case 124 may further include a second opening 128 (e.g. at the bottom of the case 124 or some other location) separate from the first opening 126. The cartridge 102 may be detached from the outer casing 450 fixed to the case through the second opening 128 without removing the mobile communications device. For example, the cartridge 102 may be detached through the second opening 128 from the outer casing 450 fixed to the case using the quarter locking mechanism 460 described above with respect to FIGS. 4A-4C. A replacement cartridge may similarly be attached to the outer casing through the second opening 128 using cap 452, and the cap 452 may be removed after replacing the cartridge. Thus, the case 124 may provide portability and convenience by allowing users to carry and use the auto injector device 100 along with their cellular phone or other communications device. Moreover, the case 124 facilitates reusability of the auto injector device by enabling users to safely remove and replace used cartridges (e.g. using the cap 452) without having to remove the mobile communications device or otherwise reach into the case 124 (e.g. through either opening 126 or 128).

Figure 5:
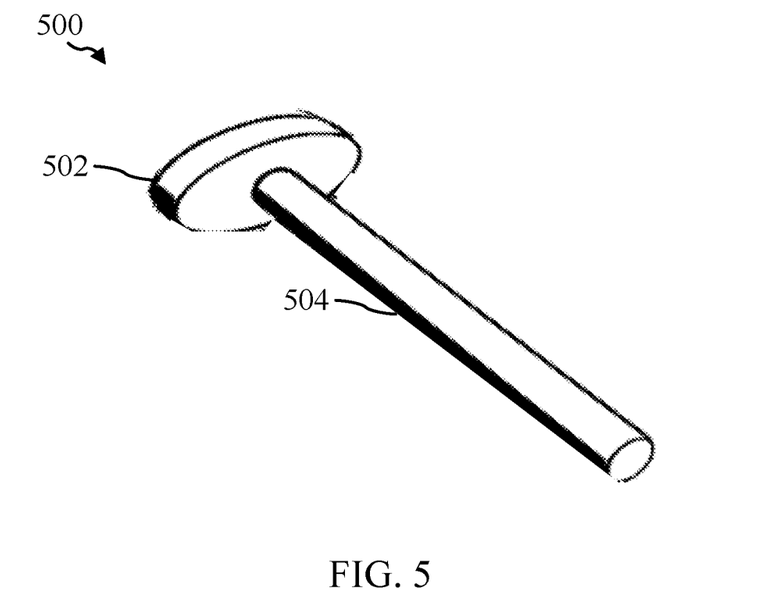
FIG. 5 is a conceptual diagram illustrating an example spring compression tool for compressing the spring of the auto injector device of FIG. 1.

Referring now to FIG. 5, when the spring 118 expands as shown in FIG. 3B to dispense the fluid 106 in the cartridge 102, the cartridge 102 may be detached from the outer casing 450 through the opening 128 of the case 124. Before a replacement cartridge 102 is attached to the outer casing 450, the spring 118 must be reset into the compressed state shown in FIG. 1 or 3A. FIG. 5 illustrates a spring compression tool 500 that may be used to facilitate the re-compression of the spring 118 after detachment of a used cartridge. The spring compression tool 500 includes a head 502 supported by a body 504. The head 502 and body 504 may be sized to exert a force against the spring 118 through the opening 128 inside the case 124 to place the spring back into the compressed state. For example, the head 502 may have a width sufficient to clear the opening 128 of the case 124, and the body 504 may have a length spanning a majority of the length of the case 124. Moreover, if the outer casing 450 containing the piston 404 illustrated in FIG. 4B is elliptical in shape, the head 502 may also be elliptical in shape to fit within the outer casing and contact the piston.

When the spring compression tool 500 is inserted through the opening 128 such that the head 502 contacts the piston 104 (e.g. the flange 110), a force may be applied by the spring compression tool 500 against the piston 104, causing the piston to compress the spring 118 (e.g. via the flange 122) against the safety chamber 112. The one or more projections 116 of the piston 104 (see FIG. 2) may subsequently contact and prevent movement of the spring, as illustrated in FIG. 3A. The safety hook 120 may also be reattached to the spring 118 to further prevent movement of the spring. For example, referring to FIG. 1, the safety hook 120 may be movably mounted to a side of the case 124 through an opening 129 or may hook around the side of the case 124 into the cavity 127, and the safety hook 120 may be pivoted, translated, or otherwise adjusted relative to the side of the case to contact (and release contact of) the spring 118. Once the spring 118 is compressed, the spring compression tool 500 may be removed from the opening 128, and a replacement cartridge may subsequently be attached.

The spring 118 may be configured such that the spring compression tool 500 may sufficiently compress the spring from the expanded state 350 to the compressed state 300 using manual force. For example, the spring may be sized such that the amount of force needed to compress the spring is less than the maximum force capable of being manually applied by a user's hand. For instance, in the case where the spring spans 3 cm in the compressed state and 5 cm in the expanded state, a force of only 30.16 N or 3.08 kg may be required to compress the spring by 2 cm, which is less than the maximum force capable of being manually applied by a user's hand (e.g. 4.6 kg). In this way, a user may easily reset the spring 118 of the auto injector device 100 simply using the spring compression tool 500 when attempting to replace a used cartridge.

Figure 6:
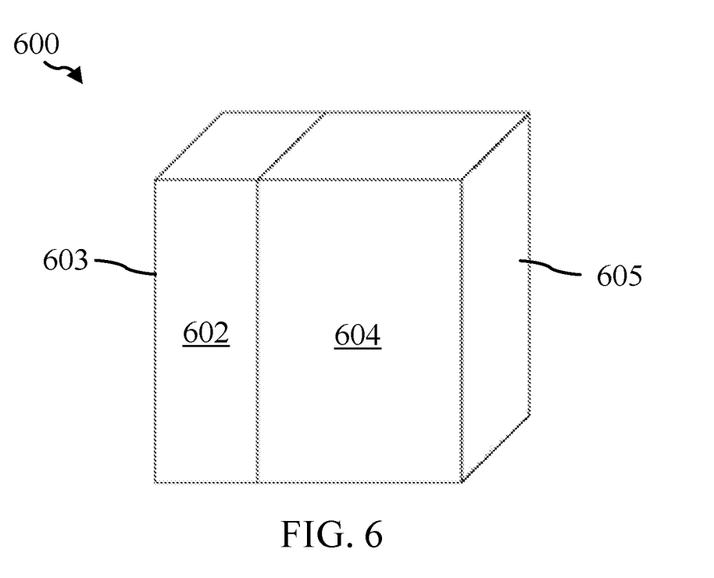
FIG. 6 is a conceptual diagram illustrating an example ratio of material used between an inner surface and outer surface of the case of the auto injector device of FIG. 1.

The case 124 may include a mixture of durable and heat-resistant materials. For instance, FIG. 6 illustrates an example diagram 600 showing a ratio of materials comprised in the case 124 of FIG. 1. For example, an outer portion 602 of the case 124 (e.g. which includes an outer surface 130, 603 of the case) may be comprised of polycarbonate or other durable material, while an inner portion 604 of the case 124 (e.g. which includes an inner surface 132, 605 of the case) may be comprised of fiberglass or other heat-resistant material. To provide thermal insulation, the inner portion 604 may be twice the size of the outer portion 602. For instance, assuming the case 124 has side width of 0.3 cm, 0.2 cm comprising the inner portion 604 may be comprised of fiberglass material while 0.1 cm comprising the outer portion 602 may be comprised of polycarbonate material. Alternatively, other ratios of heat-resistant to durable material besides 2:1 may be used. In this way, the case 124 may thermally insulate the fluid 106 in the cartridge 102 to a preferred temperature range (e.g. 20-25° C.) even in hot and cold environments, as well as protect the components of the auto injector device 100 (in addition to the mobile communications device) from drops or other impacts. Additionally, the components of the auto injector device 100 (e.g. the piston 104, safety chamber 112, and safety hook 120, etc.) may be comprised of heat-tolerant and fatigue-resistant material, such as polypropylene plastic, for added thermal insulation and protection of the auto injector device.

When a user injects the epinephrine, medication, or other fluid 106 in the cartridge 102 as described above, the user may still require treatment or hospitalization. For example, the user may still experience a severe allergic reaction or one or more side effects such as nausea, etc. Moreover, the user may also fall unconscious, or may be otherwise unable to immediately seek medical attention. Accordingly, the auto injector device 100 may include a sensor 134 attached to the case 124 which is in wireless communication with an emergency alert system.

Figure 7:
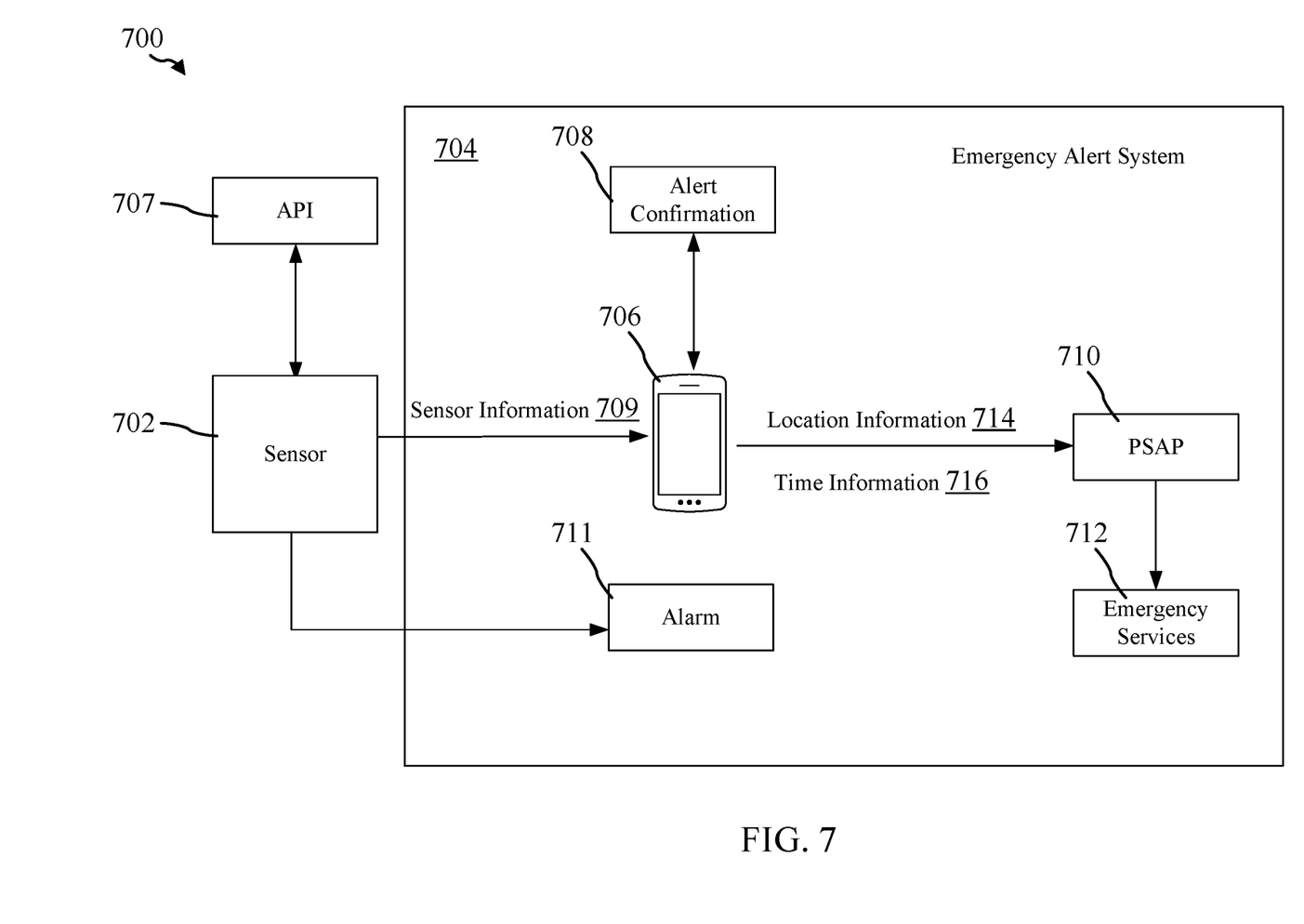
FIG. 7 is a conceptual diagram illustrating an example emergency alert system in communication with the sensor of the auto injector device of FIG. 1.

FIG. 7 illustrates an example diagram 700 of a sensor 702 in wireless communication with an emergency alert system 704. The sensor 134, 702 may be positioned in the case 124 to sense movement of the needle 108 during administration of the fluid 106 in the cartridge 102. In response to movement of the needle 108 (e.g., as described above with respect to FIG. 3A), the sensor 134, 702 may communicate with the emergency alert system 704, e.g. via the mobile communications device 706, to alert hospitals or other emergency services of the location of the mobile communications device and the time of the fluid administration. In one example, the sensor 134, 702 may wirelessly communicate with the emergency alert system 704 using Bluetooth or other wireless technology standard. For example, the sensor may communicate via cellular communication (e.g. 5G NR, 4G LTE, 3G, 2G, GSM/UMTS, CDMA One/CDMA2000, etc.), wireless distribution methods through access points (e.g. IEEE 802.11, WiFi, HiperLAN, etc.), Infra Red (IR), Bluetooth, Zigbee, or other Wireless Wide Area Network (WWAN), Wireless Local Area Network (WLAN), Wireless Personal Area Network (WPAN) technology, or comparable wide area, local area, and personal area technologies. The sensor 134, 702 may be a stand-alone sensor, or may be an on-board component of a system including one or more sensors (e.g. gyroscopes, accelerometers, magnetometers, temperature sensors, photo sensors, etc.) and/or other components (e.g. a processor, a memory, a battery, etc.).

Sensor 702 may be configured to communicate sensor information 709 in response to a detection of movement of the needle 108. For example, sensor 702 may be programmed via an application programming interface (API) 707 to transmit sensor information 709 to an application of the mobile communications device 706 in response to the movement. The application of the mobile communications device may be configured to activate an alert confirmation 708 in response to the sensor information 709. The sensor may also be configured to sound an alarm 711 (e.g. from the mobile communications device 706 and/or using a separate speaker).

The alert confirmation 708 may output an alert requesting a response within a predetermined period of time before emergency services are notified. For instance, the sensor 702 may be programmed using the API 707 to trigger the application of the mobile communications device 706 to display and/or sound an alert that an injection of epinephrine has been detected, and to request a confirmation that the detection is accurate within 5 seconds or some other time interval. The alert confirmation 708 thus may serve to prevent notification of emergency services due to false alarms (e.g. erroneous movement of the needle). If an input is received into the application (e.g. via a microphone or the display of the mobile communications device) within the predetermined period of time confirming that the detection was a false alarm, the alert is dismissed and no further action is taken.

Otherwise, if the input confirms the detection is accurate, or if no input is received at all within the predetermined period of time (for instance, the user is unconscious), the application may trigger the mobile communications device 706 to communicate with a PSAP 710 to request emergency services 712. For example, the application may trigger the mobile communications device 706 to call 9-1-1 and provide a minimum set of data (MSD) for emergency services to the PSAP. The MSD may include location information 714 indicating a location of the mobile communications device 706 or sensor 702 (e.g. Global Positioning Satellite (GPS)), and time information 716 indicating a time when injection was administered (e.g. a time stamp when the call was made to the PSAP 710). Based on the MSD, the PSAP operator may be able to dispatch emergency services 712 (e.g. paramedics, medical professionals, etc.) to the location of the user. In this way, the auto injector device 100 may allow a user to readily receive medical treatment in the event the epinephrine or other medication was ineffective or caused unanticipated side effects, thereby reducing the risk of users suffering from untreated, extreme allergic reactions.

Figure 8A:
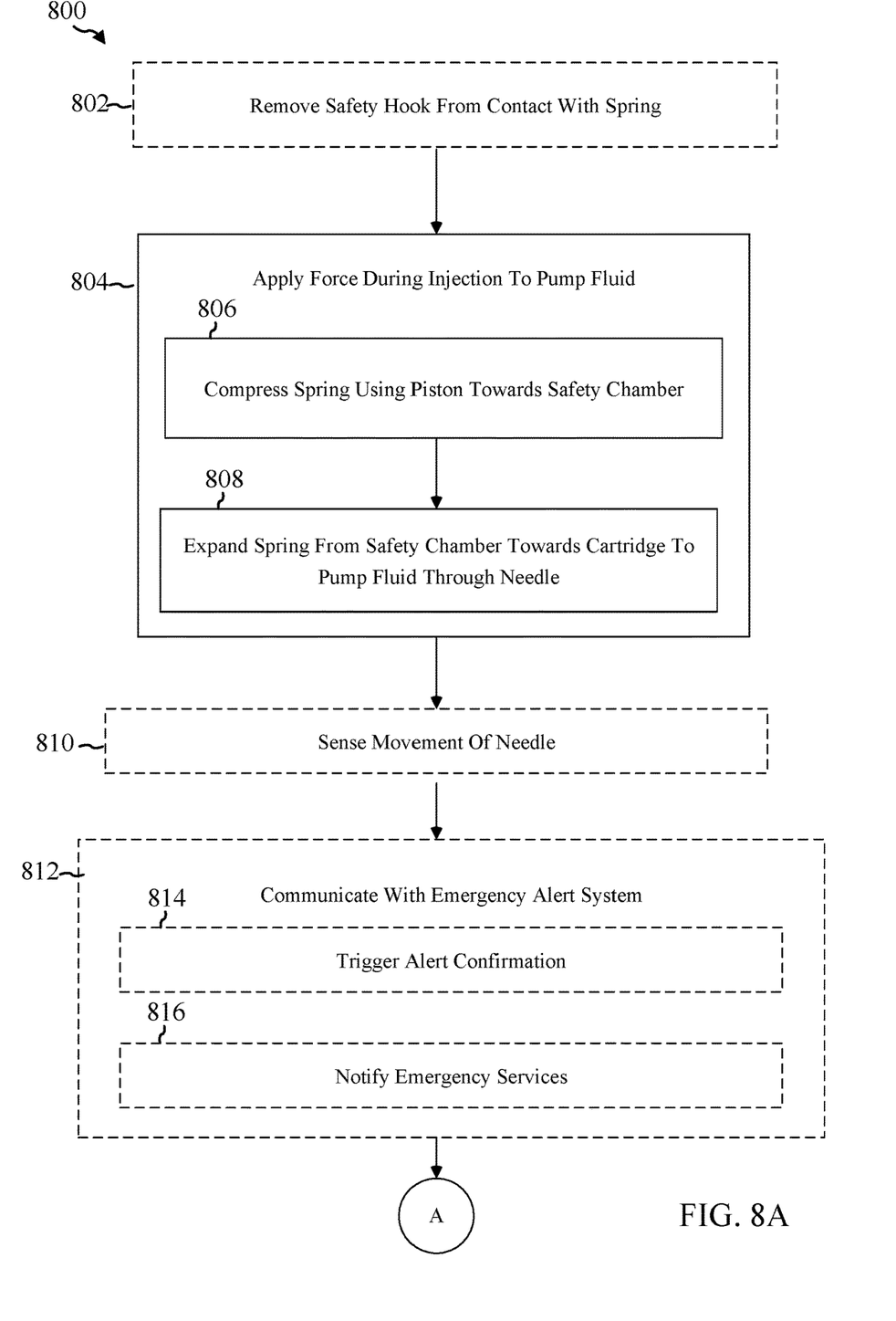
FIGS. 8A-8B is a flow chart illustrating an example method for operating the auto injector device of FIG. 1.
Figure 8B:
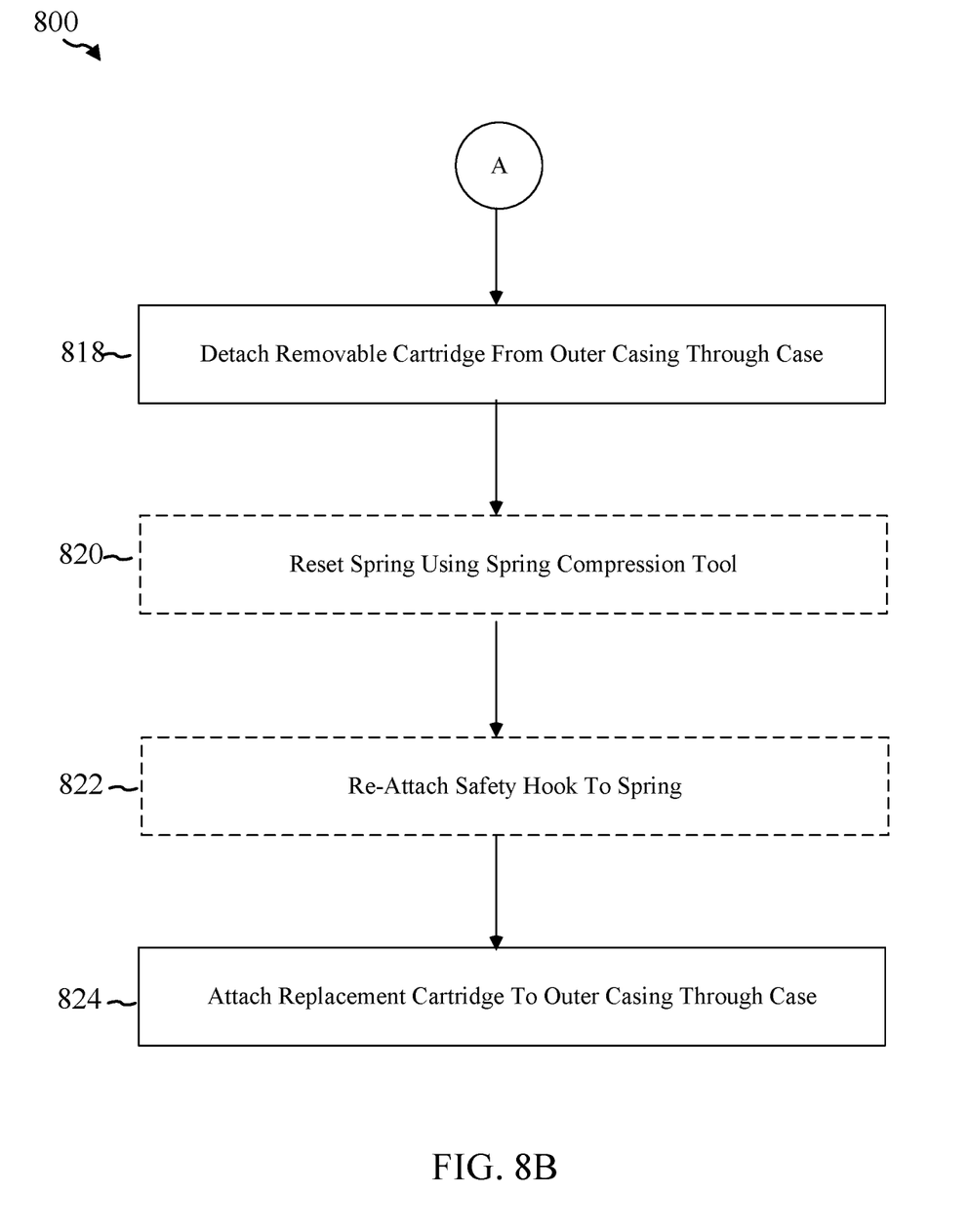

FIGS. 8A-8B are a flow diagram illustrating a method 800 of operating an auto injector device as described in the examples of FIGS. 1-7. The method may be performed by users of the auto injector device, such as consumers or medical personnel. Optional aspects are illustrated in dashed lines.

Referring to FIG. 8A, as represented by block 802, the safety hook is initially removed from contact with the spring. For example, referring to FIGS. 1 and 2, the safety hook 120 fixed to the case 124 may be pivoted, translated, or otherwise adjusted to release contact of the spring 118. For instance, the safety hook may be pulled or pivoted away from the spring 118.

As represented by block 804, a force is applied during injection of the auto injector device to pump fluid within the cartridge. For instance, as represented by block 806, the spring may compress using the piston towards the safety chamber, and as represented by block 808, the spring may expand from the safety chamber against the piston towards the cartridge to pump the fluid through the needle. For example, referring to FIGS. 1, 3A and 3B, after the user unhooks or moves the safety hook 120 away from the compressed spring 118, the user may forcefully apply the case 124 including the cartridge 102 and needle 108 against the user's thigh or other injection site. As a result, the injection site may apply an equal and opposite force against the cartridge 102, pushing the piston towards the safety chamber 112 and further compressing the spring 118. Subsequently, the portion 105 of the piston 104 including the one or more projections 116 may momentarily enter the recess 114 of the safety chamber 112, away from contact with the spring 118. As a result, the spring may become free to release the tension from compression and subsequently expand away from the safety chamber 112 towards the cartridge 102. In response to the force applied by the spring 118, the piston 104 may pump the fluid 106 within the cartridge through the needle 108 into the injection site.

As represented by block 810, the movement of the needle is sensed. For example, referring to FIGS. 1 and 7, a sensor 134, 702 may be positioned in the case 124 to sense movement of the needle 108 during administration of the fluid 106 in the cartridge 102. As described above with respect to block 804, when the user forcefully applies the case 124 including the cartridge 102 and needle 108 against the user's thigh or other injection site, the piston may force the cartridge 102 and needle 108 towards the injection site due to spring forces exerted by the spring 118 against the piston 104. The sensor 134, 702 may detect the movement of the needle, for instance, by optically detecting light no longer blocked by the position of the needle, or in other manners.

As represented by block 812, communication with an emergency alert system may be triggered. For example, as represented by block 814, an alert confirmation may be triggered, and as represented by block 816, emergency services may be notified. For instance, referring to FIGS. 1 and 7 and in response to movement of the needle 108, the sensor 134, 702 may communicate with the emergency alert system 704, e.g. via the mobile communications device 706, to alert hospitals or other emergency services of the location of the mobile communications device and the time of the fluid administration. For example, the sensor may be configured or programmed (e.g. using an application programming interface (API) 707) to trigger an application of the mobile communications device 706 to activate an alert confirmation 708 in response to sensor information 709 detecting movement of the needle 108. The alert confirmation 708 may be configured to output an alert from the mobile communications device 706 which requests a response within a predetermined period of time. If a response is received confirming the detection is accurate, or if no response is received at all within the predetermined period of time (for instance, the user is unconscious), the application may be configured to trigger the mobile communications device 706 to communicate with a PSAP 710 to request emergency services 712.

Referring now to FIG. 8B, after the cartridge is used, as represented by block 818, the removable cartridge is detached from the outer casing through the case. For instance, referring to FIGS. 1 and 4A-4D, the cartridge 102 may be detached from the outer casing 450 fixed to the case through the opening 128 without removing the mobile communications device. For example, the cartridge 102 may be detached through the opening 128 from the outer casing 450 fixed to the case using the quarter locking mechanism 460 described above with respect to FIGS. 4A-4D.

As represented by block 820, the spring is reset to its compressed state using a spring compression tool. For example, referring to FIG. 5, a spring compression tool 500 may be used to facilitate the re-compression of the spring 118 after detachment of a used cartridge. The spring compression tool 500 includes a head 502 supported by a body 504 which may be sized to exert a force against the spring 118 through the opening 128 inside the case 124 to place the spring back into the compressed state.

As represented by block 822, the safety hook may be re-attached to the compressed spring. For example, referring to FIGS. 1 and 5, after the spring compression tool 500 is inserted through the opening 128 and applies a force causing the piston to compress the spring 118 against the safety chamber 112, the safety hook 120 may also be reattached to the spring 118 to prevent movement of the spring. For example, referring to FIG. 1, the safety hook 120 may be movably mounted to a side of the case 124, and the safety hook 120 may be pivoted, translated, or otherwise adjusted relative to the side of the case to contact the spring 118. The one or more projections 116 of the piston 104 may also contact and prevent movement of the spring, as illustrated in FIG. 3A.

Lastly, as represented by block 824, a replacement cartridge is attached to the outer casing through the case. For example, referring to FIGS. 1 and 4A-4B, once the spring 118 is compressed as described with respect to block 820 and the spring compression tool 500 is removed from the opening 128, a replacement cartridge may subsequently be attached to the outer casing 450 through the opening 128 using cap 452. For example, the cartridge 102 may be attached through the opening 128 to the outer casing 450 fixed to the case using the quarter locking mechanism 460 described above with respect to FIGS. 4A-4D. The cartridge 102 is placed through the second opening 128 using cap 452 for attachment to the outer casing 450, and the cap 452 is removed after replacing the cartridge.

As a result, the present disclosure provides for reusability, portability and convenience, thermal insulation, and safety in using the auto injector device. By allowing cartridges to be detachable from the outer casing after use or expiration and new cartridges to be attachable to the outer casing for subsequent use, the auto-injector device may be cost-effectively re-used without having to replace the case, piston, spring, safety chamber, and safety hook after each use. Moreover, by fixing the piston, spring, safety chamber, and safety hook to the case, the auto injector device may be portable and convenient to carry with the user's mobile communications device, minimizing risk of a user forgetting to carry the auto injector device when needed. Furthermore, the heat-resistant material of the inner portion of the case and durable material of the outer portion of the case respectively allow the epinephrine or other medication or fluid in the auto injector device to maintain an optimal temperature notwithstanding hot and cold environments and to protect the components of the auto injector device from drops or other impact, thereby preserving the effectiveness and integrity of the auto injector device. Additionally, by incorporating a sensor fixed to the case that is configured to wirelessly communicate with an emergency alert system in response to movement of the needle, the auto injector device may provide increased safety to users who experience unconsciousness, severe allergic reactions, side effects, or other conditions from using the auto injector device.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other magnetic storage devices. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) in the United States, or an analogous statute or rule of law in another jurisdiction, unless the element is expressly recited using the phrase "means for" or, in the case of a method claim, the element is recited using the phrase "step for."

What is claimed is:

1. An auto injector device, comprising:
   a cartridge configured to contain a fluid, the cartridge including a needle;
   an outer casing attached to the cartridge and including a piston configured to pump the fluid in the cartridge through the needle in response to application of a force during injection of the auto injector device; and
   wherein the cartridge is detachable from the outer casing, and
   wherein the auto injector device is encapsulated in a case configured to hold a mobile communications device, and wherein the outer casing is fixed to the case, and wherein at least a portion of an inner surface of the case includes fiberglass material.

2. The auto injector device of claim 1, wherein the case includes an outer surface, and wherein the outer surface includes polycarbonate material.

3. The auto injector device of claim 1, further comprising:
   a sensor attached to the case and in wireless communication with an emergency alert system; and
   wherein the sensor is configured to sense movement of the needle and to communicate with the emergency alert system in response to application of the force during the injection.

4. The auto injector device of claim 1, further comprising:
   a safety chamber in the outer casing fixed to the case opposite the cartridge;
   wherein the safety chamber is configured to receive the piston in response to application of the force during the injection.

5. The auto injector device of claim 4, further comprising:
   a spring in the outer casing fixed to the case and contacting a portion of the piston between the safety chamber and the cartridge.

6. The auto injector device of claim 5, wherein the portion of the piston includes one or more projections, and wherein the safety chamber is configured to receive the one or more projections in response to application of the force during the injection.

7. The auto injector device of claim 6,
wherein the piston is configured to compress the spring towards the safety chamber in response to application of the force during the injection until the safety chamber receives the one or more projections; and
wherein the spring is configured after compressing to expand away from the safety chamber and to move the piston toward the cartridge to dispense the fluid through the needle.

8. The auto injector device of claim 5, wherein the piston includes a first flange configured to compress the spring towards the safety chamber, a second flange configured to move the cartridge in response to an expansion of the spring away from the safety chamber, and a third flange configured to dispense the fluid in the cartridge in response to the expansion of the spring.

9. The auto injector device of claim 5, further comprising:
a safety hook movably fixed to the case, wherein the safety hook is configured to prevent movement of the spring upon application of the force during the injection.

10. The auto injector device of claim 1,
wherein the case includes a first opening for receiving the mobile communications device and a second opening separate from the first opening, the cartridge being detachable from the outer casing through the second opening.

11. The auto injector device of claim 10, wherein the cartridge includes a cap, and wherein the cartridge is detachable from the outer casing through the second opening using the cap.

12. An auto injector device, comprising:
a cartridge configured to contain a fluid, the cartridge including a needle; and
an outer casing attached to the cartridge and including a piston configured to pump the fluid in the cartridge through the needle in response to application of a force during injection of the auto injector device;
wherein the auto injector device is encapsulated in a case configured to hold a mobile communications device, wherein the outer casing is fixed to the case; and
wherein the cartridge is detachable from the outer casing.

13. The auto injector device of claim 12, wherein the case includes an inner surface and an outer surface, wherein the inner surface includes fiberglass material-and wherein the outer surface includes polycarbonate material.

14. The auto injector device of claim 12, further comprising:
a sensor attached to the case and in wireless communication with an emergency alert system; and
wherein the sensor is configured to sense movement of the needle and to communicate with the emergency alert system in response to application of the force during the injection.

15. The auto injector device of claim 12,
wherein the case includes a first opening for receiving the mobile communications device and a second opening separate from the first opening, the cartridge being detachable from the outer casing through the second opening.

16. An auto injector device, comprising:
a cartridge configured to contain a fluid, the cartridge including a needle; and
an outer casing attached to the cartridge and including a piston configured to pump the fluid in the cartridge through the needle in response to application of a force during injection of the auto injector device;
wherein the auto injector device is encapsulated in a case configured to hold a mobile communications device, wherein the outer casing is fixed to the case;
wherein a sensor is attached to the case and in wireless communication with an emergency alert system;
wherein the cartridge is detachable from the outer casing; and
wherein the sensor is configured to sense movement of the needle and to communicate with the emergency alert system in response to application of the force during the injection.

17. The auto injector device of claim 16, wherein the case includes an inner surface and an outer surface, wherein the inner surface includes fiberglass material and wherein the outer surface includes polycarbonate material.

18. The auto injector device of claim 16,
wherein the case includes a first opening for receiving the mobile communications device and a second opening separate from the first opening, the cartridge being detachable from the outer casing through the second opening.

19. The auto injector device of claim 18, wherein the cartridge includes a cap, and wherein the cartridge is detachable from the outer casing through the second opening using the cap.

\* \* \* \* \*